(12) United States Patent
Asirvatham et al.

(10) Patent No.: US 7,030,260 B2
(45) Date of Patent: Apr. 18, 2006

(54) PREPARATION OF MIXED-HALOGEN HALO-SILANES

(75) Inventors: Edward Asirvatham, Chatham, NJ (US); Jeff Czarnecki, Branchburg, NJ (US); Matthew H. Luly, Hamburg, NY (US); Lawrence F. Mullan, Williamsville, NY (US); Alagappan Thenappan, Wilmington, DE (US)

(73) Assignee: Honeywell International Inc., Morristown, NJ (US)

( * ) Notice: Subject to any disclaimer, the term of this patent is extended or adjusted under 35 U.S.C. 154(b) by 214 days.

(21) Appl. No.: 10/377,367

(22) Filed: Feb. 27, 2003

(65) Prior Publication Data

US 2004/0019231 A1    Jan. 29, 2004

Related U.S. Application Data

(60) Provisional application No. 60/359,884, filed on Feb. 27, 2002.

(51) Int. Cl.
C07F 7/04    (2006.01)
(52) U.S. Cl. .................................... 556/484
(58) Field of Classification Search .............. 556/484
See application file for complete search history.

(56) References Cited

U.S. PATENT DOCUMENTS 2,894,012 A * 7/1959 Rosenberg et al. ......... 556/480

FOREIGN PATENT DOCUMENTS

| GB | 795772 | 5/1958 |
|---|---|---|
| GB | 1238932 | 7/1971 |
| JP | 61117112 | 6/1986 |
| JP | 3028371 | 2/1991 |
| JP | 2001097709 | 4/2001 |

OTHER PUBLICATIONS

Hassler et al., {Schwingungsspektren, Normalkoodinatenanalysen und Synthesen der t-Butylsilane, Journal of Organometallic Chemistry, 465 (1-2), 127-135, 1994.*
Emeleus H.J., Wilkins, C.J., Some New Ethyl and Phenyl Silicon Fluorides, J. Chem. Soc., (1944), p. 454.
Lawton E.A., Levy A., Incorporation of Adenosine-5' - Phosphate into Ribonucleic Acid, J. Amer. Chem. Soc., (1955) 77, p. 6083.
Newkirk, A.E., Preparation of the Methylfluorosilanes, J. Amer. Chem. Soc., (1946) 68, pp. 2736-2737.
Chao, T.H., Moore S.L., Lane J., Preparation of Some Cyclic Fluorosilanes, J. Organometal. Chem., (1971) 33, pp. 157-160.
Buck, H.M., Bloemhoff W., Oosterhoff J.J., The System Lewis Acid—Nitro Compound as a Strong Electron Acceptor, Tetrahedron Letters,(1960) 9, pp. 5-11.
Uhlig, W., *Synthesis of Functional Substituted Oligosilanes Based on Silyltriflate Derivatives*, Organosilicon Chemistry: From Molecules to Materials, Eds. N. Auner, J. Weiss Federal Republic of Germany, (1994), pp. 21-26.
Katzenbeisser, U., $^{29}Si^{29}Si$-*Coupling Constants of Bromo- and Iododislanes and -trisilanes $X_nSi_2H_{6-n}$ and $X_nSi_3H_{8-n}$ (X=Br,I)*, Organosilicon Chemistry: From Molecules to Materials, Eds. N. Auner, J. Weiss, Federal Republic of Germany, (1994), pp. 37-38.
Pätzold, U., *Synthesis of Heavily Halogenated Vinylsilanes*, Organosilicon Chemistry IV: From Molecules to Materials, Eds. N. Auner, J. Weiss, Federal Republic of Germany, (1996), pp. 226-228.
Hassler, K., Köll, W., *Synthesis and Spectroscopy of Phenylated and Halogenated Trisilanes and Disilanes*, Organosilicon Chemistry II: From Molecules to Materials, Eds. N. Auner, J. Weiss, Federal Republic of Germany, (1996), pp. 81-88.
Hassler, K., Schenzel, K., *Syntheses, $^{29}Si$ NMR Spectra, and Vibrational Spectra of Methylated Trisilanes*, Organosilicon Chemistry II: From Molecules to Materials, Eds. N. Auner, J. Weiss, Federal Republic of Germany, (1996), 95-100.
Pöschl, U., Siegl, H., Hassler, K., *Synthesis, Reactivity, and Spectroscopy of Phenylated Cyclotetrasilanes and Cyclopentasilanes*, Organosilicon Chemistry II: From Molecules to Materials, Eds. N. Auner, J. Weiss, Federal Republic of Germany, (1996) pp. 113-119.
Hassler, K., *Silicon-Phosphrus, -Arsenic, -Antimony, and -Bismith Cages: Syntheses and Structures*, Organosilicon Chemistry II: From Molecules to Materials, Eds. N. Auner, J. Weiss, Federal Republic of Germany, (1994), pp. 203-208.
W. Uhlig, *Convenient Approach to Novel Organosilicon Polymers*, Organosilicon Chemistry: From Molecules to Materials, Eds. N. Auner, J. Weiss, Federal Republic of Germany, (1996), pp. 703-708.
(Abstract Only Forwarded) Adamova, Y., Skachkov, A., *Reaction of Boron Trichloride with Tetraflurosilane initiated by Two Frequency-tunable Carbon Dioxide Lasers*, Khim. Vys. Energ., (1990) 24 (1), pp. 88-91.
Stanton, C., McKenzie, S., Sardella, D., Levy, R., Davidovitis, P., Boron atom reaction with silicon and germanium tetrahalides, J. Phys. Chem., 92(16) pp. 4658-4662.

(Continued)

*Primary Examiner*—Johann Richter
*Assistant Examiner*—Chukwuma Nwaonicha
(74) *Attorney, Agent, or Firm*—Deborah M. Chess

(57) ABSTRACT

The preparation of halosilanes having mixed-halogen substituents is described comprising providing an aryl-halo-silane having one more first halogens and one or more aryl groups, and substituting one or more of said aryl groups of said aryl-halo-silane with a second halogen having an atomic number greater than that of said first halogen.

26 Claims, No Drawings

OTHER PUBLICATIONS (Abstract Only Forwarded) Adamova, Y., Pankratov, A., SagitV., Skachkov, A., Stolyarova, G., Shmerling, G., *Laser Chemical Reaction of Boron Trichloride with Silicon Tetrafluoride*, Khim. Vys. Energ., (1978) 12(1), pp. 89-90.

(Abstract Forwarded) Dele-Dubois, M., Wallert, F., *Preparation and Laser-Raman Spectroscopic Indentification of Fluorochlorosilanes*, C.R. Acad. Sci., Ser. B, (1971) 272(18), pp. 1059-1061.

Airey, W., Sheldrick, G., *Preparation and Properties of Methoxytrifluorosilane, and Study of Its Reaction with Boron Trihalides*, J. Inorg. Nucl. Chem., (1970) 32(6), pp. 1827-1829.

Johansen, T., Hagen, K., Hassler, K., Tekautz, G., Stolevik, R., *1,1,2-Triiododisilane (I2HSi-SiH2I): Molecular Structure, Internal Rotation and Vibrational Properties Determine by Gas-phase Electron Diffraction, Infrared and Raman Spectroscopy, and Ab Initio Molecular Orbital- and Density Function Calculations*, J. Mol. Struct., (1999) 509 (1-3), pp. 237-254.

Kunai, A., Sakurai, T., Toyoda, E., Ishikawa, M., *Selective Synthesis of Fluoro-, Fluorohydro-, and Chlorofluorosilanes from Hydrosilanes with the Use of a CuCl2(Cul)/KF Reagent*, Organometallics, (1996) 15, pp. 2478-2482.

Database Chemabs Online! Chemical Abstracts Service, Columbus, OH, US; Kuroda Katsuhiko, et al.: "Organic fluorine-silicon compounds. XI. Preparation and Properties of silicon-functional phenylfluorosilanes and poly (phenylfluorosiloxane)" XP002265134; Database accession No. 76:60125 abstract & Kogyo Kagaku Zasshi, 74 (10), 2132-7 Coden: KGKZA7; ISBN: 0368-5462, 1971.

Patent Abstracts of Japan: vol. 0103, No. 03 (C-378), Oct. 16, 1986 & JP 61 117112 A (Central Glass Co, LTD), Jun. 4, 1986 abstract.

Database Chemabs 'Online! Chemical Abstracts Service, Columbus, OH, US; Suresh, B. S. et al: "Halogen exchange reactions of silicon tetrafluoride with phosphorus trichloride and phosphoryl chloride" XP002265135; Database accession No. 103:204851 abstract & Journal of fluorine Chemistry, 29 (4), 463-6 Coden: JFLCAR; ISSN: 0022-1139, 1985.

Patent Abstracts of Japan: vol. 2000, No. 21, Aug. 3, 2001 & JP 2001 097709 A (Tori Chemical Kenkyusho:KK), Apr. 10, 2001 abstract.

English translation of: Hassler, et al., "Vibration Spectra, Normal Coordinate Analyses and Syntheses of Tertbutylsilane tBuSiX3, X=H, D, F, Cl, Br, I", *Journal of Organometallic Chemistry*, 465 (1994) 127-135.

* cited by examiner

PREPARATION OF MIXED-HALOGEN HALO-SILANES

REFERENCE TO RELATED APPLICATION

This application is based on and claims priority to U.S. Provisional Application No. 60/359,884 filed Feb. 27, 2002, which is hereby incorporated by reference.

FIELD OF INVENTION

The present invention relates to the preparation of high-purity halo-silanes having two or more halogen moieties.

BACKGROUND

High-purity silanes having two or more different halogen moieties (referred to herein as "mixed-halogen halo-silanes") are useful sources of atomic silicon and halogens in a variety of applications. For example, trichloro-fluoro-silane ($SiFCl_3$), dichloro-difluoro-silane ($SiF_2Cl_2$), and chloro-trifluoro-silane ($SiF_3Cl$) has been used as a source of high-purity silicon in the preparation of semiconductor materials and communication-quality fiber optic materials. In addition, it has been recently reported that trifluoro-iodo-silane ($SiF_3I$) is particularly amenable to laser isotopic separation, providing isotopically pure silicon for use in the preparation of isotopically pure silicon wafers. Likewise, fluoro-iodo-silanes have been used as a source of high-purity iodine in the preparation of iodine gas lasers. Generally speaking, to be of use as an element source of silicon and halogens, the mixed-halogen halo-silane must be high purity. The term "high purity" as used herein refers to a composition comprising at least 99% by weight of one silane species and less than 0.5% by weight of non-silane impurities.

There are a number of conventional approaches for preparing high-purity mixed-halogen halo-silanes. One approach involves treating elemental silicon with mixtures of elemental halogens. For example, silicon may be treated with a mixture of $F_2$ and $Cl_2$ to produce $SiF_2Cl_2$. Another approach uses tans-halogenation reactions, in which a silicon compound containing one halide species is contacted with a metal complex containing a different halide species under conditions sufficient to induce halogen exchange between the various species. For example, $F_3SiCl$ may be produced from the irradiation of a mixture of $SiF_4$ and $BCl_3$. Other approaches combine these two approaches. For example, elemental silicon may be treated with a halide gas, e.g., $Cl_2$, and a halo-silane, e.g., $SiF_4$, to produce, among other species, a mixed-halogen halo-silane, e.g., $F_3SiCl$.

Although these approaches have been used historically to produce high-purity mixed-halogen halo-silanes, there is a general desire to reduce the costs associated with their preparation. Naturally, reducing the cost of preparing mixed-halogen halo-silanes can lead to a reduction in the cost of producing materials that use them in their preparation. Furthermore, finding new applications for these mixed-halogen halo-silanes depends upon developing economical processes for producing commercial quantities of them. Typically, the most significant barrier to economically producing high-purity mixed-halogen halo-silanes is separating the desired mixed-halogen halo-silane from the other mixed-halogen halo-silane species and byproducts formed during its preparation.

The problems associated with conventional mixed-halogen halo-silane preparation techniques tend to result from the bonding characteristics of the halogens involved. In an Si—X bond (where X is a halogen), the ability to replace one halogen with another by direct halogen substitution tends to follow the order of Si—X bond strength, Si—F>Si—Cl>Si—Br>Si—I. Thus, fluorine can replace chlorine, bromine, and iodine, chlorine can replace bromine and iodine, and bromine can replace iodine. Synthesis of mixed-halogen halo-silanes by preparative schemes based on direct replacement of one halogen species with a different halogen species are problematic because such reactions tend to lead to complete replacement of one halogen with another. Although techniques are often employed to shift the reaction's equilibrium to favor incomplete substitution of one halogen species for another, these reactions nevertheless produce a distribution of perhalogenated products.

Processes that produce a distribution of halosilane species from which a single species must be isolated do not use starting materials efficiently. In addition, because cognate halosilane species boil over a very narrow range, isolation of any one species to achieve high purity requires specialized equipment, such as a high theoretical plate distillation column, which is expensive to obtain and operate.

Therefore, there is a need for a process that uses reactions having high specific conversion of the starting material into a single product species, thereby efficiently using the starting material. The present invention fulfills this need among others.

SUMMARY OF INVENTION

The present invention provides an efficient approach for preparing a mixed-halogen halo-silane with excellent yield and selectivity. Specifically, the approach involves first preparing a silane functionalized with at least one first halogen and a specific number of aryl groups, and then substituting the aryl groups with a second halogen having a lower bond strength (i.e., higher atomic number) than the first halogen. Applicants have found that aryl group substitution provides a convenient and predictable mechanism through which to introduce lower bond strength halogens into a silane. Therefore, the approach of the present invention uses this mechanism to add a halogen substituent of relatively-low bond strength to a silane after it has been functionalized with a relatively-high bond strength halogen. This is a significant departure from prior art approaches which tend to functionalize the silane with lower bond strength halogensfirst and then rely on halogen exchange to displace a portion of the lower bond strength halogens with higher bond strength halogens to arrive at the desired mixed-halogen halo-silane.

The approach of the present invention offers a number of significant advantages over prior art approaches. First, the approach does not rely on unpredictable halogen exchange between a lower bond strength halogen and a higher bond strength halogen to form a desired mixed-halogen halo-silane. As mentioned above, such an approach typically results in a distribution of mixed-halogen halo-silane species—i.e., silanes having different combinations of halogens. Rather, the approach of the present invention relies on the predictable substitution of aryl groups by the lower bond strength halogens, resulting in a narrow distribution of mixed-halogen halo-silane species. This narrow distribution of product eliminates the prior art difficulty of isolating the mixed-halogen halo-silane from a wide distribution of other mixed-halogen halo-silanes species, thereby increasing yield and efficiency.
}

Additionally, using an aryl-halo-silane to prepare the final product offers a number of its own advantages. For example, since the process of the present invention provides for the predictable substitution of aryl groups by the lower bond strength halogens, the aryl functionality of the aryl-halo-silane essentially determines the number of lower bond strength halogens on the end product. This is significant since silanes, which are functionalized in varying degrees with aryl groups, are readily isolated using traditional distillation techniques, especially compared to permutations of mixed-halogen halo-silanes which tend to have similar properties and, thus, are not readily separable. Accordingly, rather than attempting to isolate a particular mixed-halogen halo-silane from its other species, the purification can essentially be done before its preparation by readily isolating the particular aryl-halo-silane from which it is prepared. This way, the isolated aryl-halo-silane will contain the number of aryl groups corresponding to the desired number of lower bond strength halogens on the final product.

Furthermore, depending upon the desired halogen composition of the end product, it may be preferable to effect a halogen exchange with an intermediate aryl-halo-silane. For example, if the intermediate aryl-halo-silane is an aryl-chloro-silane but the desired high-bond strength halogen is fluorine, then a halogen exchange between the chlorine and fluorine can be performed to provide an aryl-fluoro-silane. Halogen exchange can be a predictable, high yield reaction, especially if a lower bond strength halogen is exchanged for a higher bond strength halogen. Thus, by using an aryl-halo-silane, the present invention allows for a highly reliable and efficient reaction to select the high-bond strength halogen of the mixed-halogen halo-silane end product.

Other advantages of the present invention may be obvious to one skilled in the art in light of this disclosure.

Accordingly, one aspect of the claimed invention is a process for preparing a mixed-halogen halo-silane from an aryl-halo-silane by substituting the aryl groups with the lower bond strength halogens. In a preferred embodiment, the process comprises (a) providing an aryl-halo-silane comprising one or more first halogens and one or more aryl groups; and (b) substituting one or more of the aryl groups of said aryl-halo-silane with a second halogen having an atomic number greater than that of said first halogen. Preferably, providing said aryl-halo-silane comprises providing an intermediate aryl-halo-silane having one more third halogens and then exchanging at least a portion of said one or more third halogens of said intermediate aryl-halo-silane with one or more first halogens of a lower atomic number than that of said third halogen to form said aryl-halo-silane. Furthermore, in the preferred embodiment, providing said aryl-halo-silane further comprises isolating the aryl-halo-silane based on the number of aryl groups before substituting the aryl groups.

DETAILED DESCRIPTION OF PREFERRED EMBODIMENTS

The present invention relates to a process for producing halo-silanes that contain two different species of halogen moieties (mixed-halogen halo-silanes) in high purity and in high yield. The process comprises: (1) providing an aryl-halo-silane having one or more first halogens and one or more aryl groups, and (2) substituting at least some of the aryl groups with a second halogen which has an atomic number greater than that of the first halogen substituents. Each of these two basic steps is considered in more detail below. For purposes of simplicity, the process will be considered often with respect to just a mono-silane compound, however, it should be understood that the process of the present invention may be practiced with monosilanes and polysilanes. Additionally, although only mixed-halogen halo-silanes are considered in detail herein, the process of the present invention may be practiced to prepare halo-silanes comprising just one halogen moiety.

1. Provision of Aryl-halo-silane

The first step in the process of the present invention is the provision of an aryl-halo-silane. In a preferred embodiment, the step of providing an aryl-halo-silane comprises providing a compound of Formula (1):

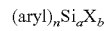   Formula (1)

wherein:
a=an integer from 1 to 10;
$1 \leq n \leq 2a+1$;
b=(2a+2−n);
X is independently selected from F, Cl, and Br, and I; and
aryl is an aryl or alkylaryl moiety.

Preparation of the aryl-halo-silane is represented schematically in Equation (1) for a monosilane.

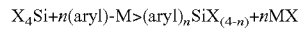   Equation (1)

where (aryl)-M is an organometallic reagent.

The reaction of Equation (1) is art-recognized displacement of a halogen moiety from a silicon atom with the subsequent formation of an organo-silane by an organometallic reagent in which the organic moiety has strong Lewis base character. An example of this is the formation of an organo-silane by treatment of a silicon halide with a Grignard reagent. It will be appreciated that other organometal reagents, for example, lithium reagents, can also be employed in a reaction of this type. It will be appreciated that the reaction is applicable to mono- and polysilanes.

It will be appreciated that even though the reaction will produce a distribution of possible substitution patterns, it is known in the art to adjust the reaction variables to favor aryl group replacement of one, two, or three halogen moieties of the halo-silane starting materials, as the need for the various intermediate materials dictates.

It should also be noted that by utilizing a starting material that is perhalogenated with all of one species of halogen substituent, the starting material can be economically provided in a highly pure state. For example, highly purified tetrachlorosilane (silicon tetrachloride) is an article of commerce.

The aryl moiety of the organometallic reagent can be any aromatic moiety, for example, phenyl, alkyl-substituted phenyl, biphenyl, aromatic heterocycles (e.g., pyrrolyl), and moieties based on fused aromatic ring compounds (e.g., napthyl). Preferably, it is chosen based on three considerations: 1) ease of separation of the aryl-halo-silane product from the reaction mixture of Equation (1) (step 1, above) and of the aryl by-product from the mixed-halogen halo-silane produced in step 2, above; 2) the ability of the organo-silane bond to withstand subsequent processing conditions (e.g., as described below, the halogen substitution step in which a purified aryl-halo-silane has some or all of the halogen substituents replaced by another halogen of lower atomic number); and 3) reactivity effects on the formation of the aryl-halo-silane afforded by the choice of the aryl group and its influence on the conversion of the aryl-halo-silane to a mixed-halogen halo-silane. Each of these considerations is considered in more detail below.

With regard to the first consideration, as the aryl moiety becomes larger, the various silane adducts tend to boil over a wider temperature range and at a higher temperature. In addition, the aryl moiety of the aryl-halo-silane intermediate is liberated during aryl substitution (step 2) as the hydrogen adduct. For example, a phenyl moiety is liberated as benzene. Depending upon the nature of the mixed-halogen halo-silane produced in the reaction, byproducts of a lower or higher boiling point may be required. With regard to the third point, reactivity advantages which can be realized by careful selection of the aryl substituent are exemplified by selection of a large aryl moiety which, after the first halogen substitution, will tend to block the approach of a subsequent organo-metal reagent to the mono-substituted halo-silane, thus suppressing the formation of multiply or completely aryl substituted silanes. Reactivity advantages may be realized by selection of the substituents on the aryl moiety, for example, fluorine or alkyl substituents which will affect the electron density on the silane atom to which it is a substituent, and thereby alter the reactivity of the silicon atom toward halogen exchange or substitution.

It should be noted that in the formation of the aryl-halo-silane intermediate according to Equation (1), the halo-silane starting material can be chosen to yield a species which incorporates the halogen having the lowest atomic number of the halogens appearing in the product. Thus, for example, if $X_n SiCl_{(4-n)}$ is the desired product, and X—Si is iodine or bromine, the first reaction can utilize $SiCl_4$ as the starting material, and isolate the species having a number of aryl substituents equal to the desired value of "n" in the product silane during workup of the reaction product mixture for conversion to product. In such a case, a subsequent step, described below, in which the halogen substituents of the aryl-halo-silane intermediate are replaced by a halogen substituent of the lowest atomic number that will appear in the product compound will not be necessary, since it is already present in the compound at this stage of the process.

When fluorine substituents on the silane are desired, especially for the case in which the product is monofluoro substituted, the high-bond strength of the Si—F bond mitigates against use of tetrafluorosilane as a starting material from a standpoint of efficient utilization of the starting material and obtaining a narrow product distribution. To overcome this problem, the process of the present invention can include a step in which a chlorosilane is employed to provide an intermediate aryl-halo-silane that has chlorine substituents bonded to the silicone atom(s) of the intermediate where it is desired to have a fluorine atom. These chlorine atoms are then exchanged for fluorine atoms, as described below.

Thus, it may be preferable to modify the aryl-halo-silane such that it comprises the desired halogens. For example, it may be preferable to convert an aryl-Z-silane to an aryl-X-silane as described in Equation (2):

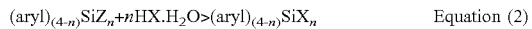
$(aryl)_{(4-n)}SiZ_n + nHX \cdot H_2O > (aryl)_{(4-n)}SiX_n$   Equation (2)

where:

Z is a halogen other than X.

Preferably, X has an atomic number lower than Z. For example, it may be preferable to convert an aryl-chloro-silane to an aryl-fluoro-silane. The reaction can be carried out by treating the intermediate aryl-halo-silane compound from Equation (1), under aqueous conditions, with the hydrogen halide acid having the halide moiety desired in the product. In general, conditions described in Tetrahedron Letters, 1960, 5, page 11, can be employed to realize this transformation. Typically, a 40% acid solution is employed at low temperature for several hours. Additionally, it will be appreciated that anhydrous hydrogen fluoride gas can be used to fluorinate the aryl-halo-silane, yielding aryl-fluoro-silane. The reaction conditions necessary to provide such halogen exchange are known to those of skill in the art.

The products of the reaction of Equation (1), $(aryl)_n SiX_{(4-n)}$ for n=1–4, boil over a broad range, and can therefore be isolated in a high-purity form by ordinary fractional distillation methods. In contrast, it is worthwhile to note that a mixture of $Y_n SiX_{(4-n)}$ where Y is a second halogen in place of the aryl group, boil over a narrow range and, unlike a mixture of the cognate aryl species, cannot be separated in high purity by ordinary fractional distillation. Thus, the mixture of aryl-halo-silanes produced by the first reaction provides a precursor which is easily isolated in high purity, and can be used in the high specificity aryl substitution reaction (described below) to produce a high-purity mixed-halogen perhalogenated silane product.

2. Substitution of Aryl Groups with Halogen

The mixed-halogen halo-silane is prepared substituting at least some of the aryl groups with a second halogen which has an atomic number greater than that of the first halogen substituents. In a preferred embodiment, the aryl groups of the silane of Formula (1) are substituted with second halogens to form the mixed-halogen halo-silane of Formula (2):

$(aryl)_{n-z}Si_a X_b Y_z$,   Formula (2)

where:

$1 \leq z \leq n$.

Preferably, each occurrence of X in the compound is the same and each occurrence of Y in the compound is the same. Additionally, if a=b=2 and X is F, then it is preferred that both fluorine moieties are bonded to the same silicon atom. It is also preferred that z=n, that is that all of the aryl groups are substituted for halogens in the second step of the process.

The aryl substitution reaction is presented in Equation (3) for the case in which a perhalogenated monosilane product is formed:

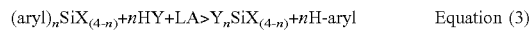
$(aryl)_n SiX_{(4-n)} + nHY + LA > Y_n SiX_{(4-n)} + nH\text{-aryl}$   Equation (3)

where aryl is an aryl or alkylaryl moiety,

X and Y are independently selected from F, Cl, and Br, and I such that the atomic number of X is less than Y; and LA is a Lewis acid.

The reaction of Equation (3) converts the isolated and purified intermediate aryl-halo-silane, whether directly from the reaction of Equation (1) or after having had the halogen groups substituted by the reaction of Equation (2) described above, to a halogenated silane containing halogen moieties comprising two different halogen species. In the conversion, the aryl moieties are substituted by halogen moieties. The reaction comprising the method of conversion can be carried out using gas-phase reagents bubbled through the liquid starting material, or it can be carried out in anhydrous conditions in a solvent, for example, pentane.

It will be appreciated that this reaction will be equally effective when applied to any aryl-silane species containing moieties of one halogen species in the formation of halogenated silanes containing more than one species of halogen, whether the product silane is perhalogenated or not, and equally applicable to mono- and polysilane species.

Lewis acids catalyze the reaction comprising the method of converting aryl-silane moieties to halo-silane moieties of the present invention. Any Lewis acid which is capable of coordinating the hydrogen halide used in the reaction, and thereby promote dissociation of the hydrogen from the halide, can be used to catalyze the reaction. The Lewis acid can be generated in situ, for example, generation of (CH3) 3N+H.Cl— by contacting HCl and trimethyl amine, where the Lewis acid is the ammonium ion. Preferred Lewis acids are of the formula $MY_z$, where Y is selected from Cl, Br, and I, and M is a metal that can coordinate at least z+1 halogen moieties and has Lewis acid properties when coordinated with z halogen moieties. That is, z is the number of halogen moeities coordinated in the neutral metal complex. In the present invention, the most preferred Lewis acids are aluminum trihalides.

When the starting silane is a gas, the reaction can be run by contacting the two vapor phase reactants over the Lewis acid (which is typically a solid). When the starting silane is a liquid, the hydrogen halide can be bubbled through the liquid, with the reactants contacting the Lewis acid present as a solid phase or dissolved in the liquid phase.

Critical to the method of converting aryl-silicon bonds to halo-silicon bonds of the present invention is that the conditions in which the reactants are contacted are anhydrous.

EXAMPLES

The process of the present invention is illustrated below at two critical stages by the first example, conversion of a commercially available phenyl-chloro-silane to the corresponding phenyl-fluoro-silane, thus illustrating the second reaction in the process, and by the second to fifth examples, the conversion of the phenyl-fluoro-silane to the corresponding iodo-fluoro-silane, (Examples 2 to 4) and chloro-fluoro-silane (Example 5) thus illustrating the third reaction in the process, the method of converting aryl-silicon bonds to halo-silicon bonds.

The phenyl-trichloro-silane starting material from which the phenyl-trifluoro-silane was prepared in the first example was obtained commercially as an article of commerce. All other reagents used were standard laboratory reagent grade materials. The phenyl-trifluoro-silane prepared in the first example was used in reactions of the second to fifth examples.

The products of the examples were analyzed by gas chromatography/mass spectrometry using a GC/MS equipped with a DB-5 column.

Example 1

Preparation of Phenyl-trifluoro-silane

Into a reaction vessel equipped with a stirring device and a dropping funnel was placed phenyl-trichloro-silane. This was cooled to 0° C. in an ice bath. A super-stoichiometric amount of HF relative to the chloride content of the phenyl-trichloro-silane in the form of a 40% hydrogen fluoride solution was placed into the dropping funnel and added dropwise to the silane with stirring. Temperature was maintained at 0° C. and stirring was continued. At the end of the reaction period, the reaction product was worked up by distillation and isolation of the phenyl-trifluoro-silane.

This example demonstrates that aryl-silicon bonds in an aryl-halo-silane are sufficiently robust to withstand the conditions required to convert the halogen-silicon bonds from on species of halogen to another. Further, it demonstrates that by starting with a pure aryl-halo-silane, a different pure species can be obtained.

There follows three examples in which the phenyl-trifluoro-silane prepared above was used as a starting material in the preparation of iodo-trifluoro-silane (Examples 2–4) and one example in which it was used as a starting material in the preparation of chloro-trifluoro-silane (Example 5). The conversion of the phenyl-trifluoro-silane was carried out according to the method of the present invention for the substitution by halogen moieties of aryl moieties in silanes. In Examples 2, 3 and 5, the reaction is conducted with neat reactants (no solvent), in Example 4, the reaction is conducted in the presence of pentane as a solvent. The reactions of Examples 2–4 were conducted without heating the reaction mixture (ambient temperature), this is to say at a temperature of about 25° C. (room temperature). The reaction of Example 5 was carried out at sub-ambient temperature.

Examples 2 through 4

Preparation of Iodo-Trifluoro-Silane

In all three examples, the reaction was conducted using the same procedure. Anhydrous HI was produced in a gas generating apparatus comprising a flask equipped with a pressure equalized dropping funnel and a gas outlet by placing phosphorous pentoxide into the vessel and treating it with dropwise addition of a 57.1 wt. % aqueous solution of the acid contained in the dropping funnel. The HI vapors thus generated were conducted from the gas generating apparatus to a reaction vessel consisting of a three neck flask equipped with a thermometer, a gas inlet tube, and a dry ice condenser. The flask contained a stirring device and the reaction mixture comprising phenyl-trifluoro-silane and aluminum triiodide, the Lewis acid catalyzing the reaction, and, in Example 4, pentane as a solvent. In the three examples, HI was bubbled through the reaction mixture during the course of the reaction until it ceased being generated by the gas generating apparatus. The reaction mixture was stirred throughout the reaction period, and the reaction mixture was refluxed, using the dry ice condenser to condense and return the volatile components to the reaction vessel. At the end of the reaction, the reaction mixture was analyzed for yield and purity of iodo-trifluoro-silane without separation of the components from the reaction mixture.

Example 2

Room Temperature Conversion of Phenyl-Trifluoro-Silane

The HI generating apparatus described above was charged with 17.5 grams of phosphorous pentoxide in the flask and 14.0 g of aqueous HI in the dropping funnel. The reaction vessel described above was charged with 0.4 g of $AlI_3$ and 8.1 g of the phenyl-trifluoro-silane prepared in Example 1. The vessels were purged with dry nitrogen and HI generation was begun, as described above. The HI vapors were passed through the silane in the reaction vessel, and refluxing commenced. The reaction was continued for 30 minutes at ambient temperature. At the end of this time, the reaction mixture was isolated and analyzed by GC/MS which indicated a yield, based on starting silane converted, of 49% iodo-trifluoro-silane.

Example 3

Elevated Temperature Conversion of Phenyl-Trifluoro-Silane

The HI generating apparatus described above was charged with 32.6 grams of phosphorous pentoxide in the flask and 22.5 g of aqueous HI in the dropping funnel. The reaction vessel described above was charged with 2.6 g of $AlI_3$ and 10.1 g of the phenyl-trifluoro-silane prepared in Example 1. The vessels were purged with dry nitrogen and HI generation was commenced, as described above, and passed through the reaction mixture in the reaction vessel. The reaction mixture was heated on a hot water bath with stirring to about 30° C. over a period of 15 minutes. The reaction mixture was held at this temperature for about 3 hours, during which the reaction mixture refluxed. At the end of this time, the reaction mixture was isolated and analyzed by GC/MS which indicated a yield, based on starting silane converted, of 80% iodo-trifluoro-silane.

Example 4

Room Temperature

Conversion of Phenyl-Trifluoro-Silane in a Solvent

The HI generating apparatus described above was charged with 17.1 grams of phosphorous pentoxide in the flask and 13.5 g of aqueous HI in the dropping funnel. The reaction vessel described above was charged with 0.4 g of $AlI_3$ and 8.1 g of the phenyl-trifluoro-silane prepared in Example 1, and 20.2 grams of n-pentane. The vessels were purged with dry nitrogen and HI was generated, as described above, and passed through the silane/pentane solution in the reaction vessel with stirring. The reaction mixture was left to reflux for one hour at ambient temperature. At the end of this time, the reaction mixture was isolated and analyzed by GC which indicated a yield, based on starting silane converted, of 20% iodo-trifluoro-silane.

Example 5

Conversion of Phenyl-Trifluoro-Silane to Chloro-Trifluoro-Silane

Into a heavy walled stainless steel cylinder of 300 ml volume was placed 18.3 g of $AlCl_3$ under a nitrogen purge. In one addition, 55 g of the phenyl-trifluoro-silane prepared above was added to the cylinder. The cylinder was sealed by fitting a gauge and valve assembly. The cylinder was then pressurized to 200 psig with anhydrous HCl and sealed. The sealed cylinder was placed in an ice bath and manually shaken every 15 minutes for the duration of the reaction period. At the end of 27 hours, the cylinder was fitted with a transfer line, connecting the reaction cylinder with a receiving cylinder. The receiving cylinder and transfer line were purged with nitrogen, sealed, and the receiving cylinder placed in an ice bath. The reaction cylinder was then warmed to 38 degrees C. by placing in a water bath and the valve opened, flash distilling the contents of the reaction cylinder into the receiving cylinder. The contents of the receiving cylinder were analyzed and found to be about 99.2% $SiF_3Cl$ with a yield of about 98 mole % based on the starting silane.

These examples demonstrate that the aryl-halo-silane can be converted to a halo-silane having two different species of halogen moiety under a variety of conditions that yield a single product from the starting aryl-halo-silane.

What is claimed is:

1. A process for preparing a mixed halo-silane comprising the steps of:
   (a) providing an intermediate aryl-halo-silane having one or more third halogens and one or more aryl groups;
   (b) exchanging at least a portion of said one or more third halogens of said intermediate aryl-halo-silane with one or more first halogens to produce an aryl-halo-silane having one or more first halogens and one or more aryl group; and
   (c) substituting one or more of said aryl groups of said aryl-halo-silane with a second halogen having an atomic number greater than that of said first halogen.

2. The process of claim 1, wherein said third halogen has an atomic number greater than said first halogen.

3. The process of claim 2, wherein said first halogen is fluorine, said second halogen is one of chlorine, bromine, or iodine, and said third halogen is chlorine.

4. The process of claim 3, wherein said aryl group is a phenyl group.

5. The process of claim 4, wherein said aryl-halo-silane is an aryl-fluoro-silane selected from the group consisting of phenyl-trifluoro-silane, diphenyl-difluoro silane, and triphenyl-fluorosilane.

6. The process of claim 1, wherein providing said intermediate aryl-halo-silane comprises:
   preparing said intermediate aryl-halo-silane by providing a halo-silane having two or more third halogens and replacing a portion of said two or more third halogens with one or more aryl groups to form said intermediate aryl-halo-silane.

7. The process of claim 6, wherein said halo-silane is a perhalogenated halo-silane.

8. The process of claim 6, wherein said halo-silane is $SiZ_4$, where Z is selected from Cl, Br, and I, and wherein preparing said intermediate aryl-halo-silane comprises reacting an aryl-metal reagent with $SiZ_4$.

9. The process of claim 8, wherein said halo-silane is $SiCl_4$.

10. The process of claim 1, wherein providing said intermediate aryl-halo-silane comprises:
    substantially isolating it from a mixture of aryl halosilanes based on its number of aryl groups.

11. A process for preparing a mixed halo-silane comprising the steps of:
    (a) providing an aryl-halo-silane having one or more first halogens and one or more aryl groups; and
    (b) substituting one or more of said aryl groups of said aryl-halo-silane with a second halogen having an atomic number greater than that of said first halogen,
    wherein providing said aryl-halo-silane comprises preparing said aryl-halo-silane by providing a halo-silane comprising two or more first halogens and replacing a portion of said two or more first halogens with one or more aryl groups to form said intermediate aryl-halo-silane.

12. The process of claim 11, wherein preparing said aryl-halo-silane comprises reacting an aryl magnesium halide with $SiF_4$.

13. The process of claim 11, wherein providing said aryl-halo-silane comprises:
    substantially isolating it from a mixture of aryl halosilanes based on its number of aryl groups.

14. The process of claim 1, wherein substituting one or more aryl groups comprises contacting said aryl-halo-silane with HCl in the presence of a Lewis acid of the formula $(CH_3)_3N^+H$.

15. A process for preparing a mixed halo-silane comprising the steps of:
(a) providing an aryl-halo-silane having one or more first halogens and one or more aryl groups; and
(b) substituting one or more of said aryl groups of said aryl-halo-silane with a second halogen having an atomic number greater than that of said first halogen, wherein said aryl-halo-silane has the formula:

$(aryl)_n Si_a X_b$, and wherein said mixed halo-silane has the formula:

$(aryl)_{n-z} Si_a X_b Y_z$, wherein
a=an integer from 1 to 10;
$1 n \leq 2a+1$;
b=(2a+2−n); and
X and Y are independently selected from F, Cl, and Br, and I;
the atomic number of X is less than Y; and
$1 \leq z \leq n$.

16. The process of claim 15, wherein, when a=b=2 and X is F, then both fluorine moieties are bonded to the same silicon atom.

17. The process of claim 15, wherein X and Y are the same for each occurrence.

18. The process of claim 17, wherein a=1.

19. The process of claim 18, wherein z=n.

20. The process of claim 15, wherein the aryl groups are substituted by treatment with a halo-acid of the formula HY in the presence of a Lewis acid.

21. The process of claim 20, wherein said Lewis acid is a metal halide of the formula:

$MY_z$, wherein
M is a metal having a coordination number greater than one, and
"z" is the number of moieties coordinated in a neutral complex of the metal.

22. The process of claim 1, wherein said production of an aryl-halo-silane having one or more first halogens and one or more aryl groups comprises the sub-steps:
(i) providing a halo-silane having at least two halogen moiety, said halogen moiety being the same and selected from Cl, Br, and I;
(ii) forming a first intermediate product mixture comprising an intermediate aryl-halo-silane by substituting one or more of said halogen substituents of said halo-silane with a phenyl group; and
(iii) replacing the halogen substituents of said portion with fluorine substituents, thereby forming a phenyl-fluoro-silane;
and wherein step (c) comprises contacting said phenyl-fluoro-silane with HX under anhydrous conditions in the presence of a Lewis acid, where X is selected from Cl, Br, and I, to form said mixed-halogen halo-silane.

23. The process of claim 22, wherein phenyl-fluoro-silane is phenyl-trifluoro silane and HX is HI, and wherein contacting said phenyl-fluoro-silane with HX comprises contacting said phenyl-trifluoro silane with said HI in the presence of $AlI_3$ at a temperature above about 29° C. to form iodo-trifluoro silane.

24. The process of claim 23, wherein at least 80% of phenyl-trifluoro silane is converted to said iodo-trifluoro silane.

25. The process of claim 23, wherein 0.9 mole equivalents of benzene based on $(phenyl)SiF_3$ are produced.

26. The process of claim 22, wherein phenyl-fluoro-silane is phenyl-trifluoro silane and HX is HCl, and wherein contacting said phenyl-fluoro-silane with HX comprises contacting said phenyl-trifluoro silane with said HCl in the presence of $AlCl_3$ to form chloro-trifluoro silane.

* * * * *